United States Patent [19]
Kumar et al.

[11] Patent Number: 5,843,956
[45] Date of Patent: Dec. 1, 1998

[54] SUBSTITUTED N-ARYLMETHYL AND HETEROCYCLYLMETHYL-1H-PYRAZOLO (3,4-B) QUINOLIN-4-AMINES AND COMPOSITIONS AND METHODS OF USE THEREOF

[75] Inventors: Virendra Kumar, Paoli, Pa.; John Alan Dority, Jr., West Haven, Conn.

[73] Assignee: Sanofi, Paris, France

[21] Appl. No.: 801,679

[22] Filed: Feb. 18, 1997

Related U.S. Application Data

[62] Division of Ser. No. 402,267, Mar. 10, 1995, Pat. No. 5,614,530.

[51] Int. Cl.$^6$ .......................... A61K 31/47; A61K 31/495; C07D 215/46; C07D 471/04
[52] U.S. Cl. .................. 514/293; 514/232.8; 514/253; 514/256; 544/115; 544/238; 544/333; 544/405; 546/82
[58] Field of Search ...................... 544/115, 238, 544/333, 405; 546/82; 514/253, 256, 232.8, 293

[56] References Cited

U.S. PATENT DOCUMENTS 4,013,665  3/1977  Crenshaw et al. ............... 260/288 CF

OTHER PUBLICATIONS

Stein et al, J. Med. Chem. 1970, 13(10), 153–155.

Zikan et al, Chem. Abstracts 108:204613K 1988.

Zikan et al, Chem. Abstracts 106:138447q 1987.

Radl et al, Chem. Abstracts 106:18429P 1987.

Radl et al, Chem. Abstracts 105:226434T 1986.

Crenshaw et al, J. Med. Chem., 1976, 19(2), 626–275.

Abrams J. The American Journal of Medicine 91 (suppl 3C), 1065–1125, Sep. 1991.

Nicholson C. D. et al. TIPS 12, 19–27, Jan. 1991.

*Primary Examiner*—Evelyn Huang
*Attorney, Agent, or Firm*—Michael D. Alexander; Mary P. Bauman; Paul E. Dupont.

[57] ABSTRACT

Substituted N-arylmethyl and heterocyclylmethyl-1H-pyrazolo[3,4-b]quinolin-4-amines, pharmaceutical compositions containing them and methods for a) effecting c-GMP-phosphodiesterase inhibition, b) treating heart failure and/or hypertension, c) reversing or reducing nitrate-induced tolerance and d) treating angina pectoris, congestive heart disease and myocardial infarction utilizing them.

31 Claims, No Drawings

SUBSTITUTED N-ARYLMETHYL AND HETEROCYCLYLMETHYL-1H-PYRAZOLO (3,4-B) QUINOLIN-4-AMINES AND COMPOSITIONS AND METHODS OF USE THEREOF

CROSS-REFERENCE TO RELATED APPLICATIONS

This application is a division of application Ser. No. 08/402,267, filed Mar. 10, 1995, U.S. Pat. No. 5,614,530.

BACKGROUND OF THE INVENTION (a) Field of the Invention

The invention relates to substituted N-arylmethyl and heterocyclylmethyl-1-H-pyrazolo[3,4-b]quinolin-4-amines, to pharmaceutical compositions containing them and to methods for a) effecting c-GMP-phosphodiesterase inhibition, b) treating heart failure and/or hypertension, c) reversing or reducing nitrate-induced tolerance and d) treating angina pectoris, congestive heart disease and myocardial infarction utilizing them.

(b) Information Disclosure Statement

Crenshaw et al., J. Med. Chem. 1976, 19(2), 262–275, disclose a series of N-substituted-1,3-dimethyl-1H-pyrazolo [3,4-b]quinolin-4-amines which are said to be useful as interferon inducing agents. Specifically disclosed are N-cyclopropyl, N-tricyclo[3.3.1.1$^{3,7}$]dec-1-yl, N-(3-pyridinylmethyl), and N-[[2-(dimethylamino)phenyl] methyl]-1,3-dimethyl-1H-pyrazolo[3,4-b]quinolin-4-amines, as well as N-(1,3-dimethyl-1H-pyrazolo[3,4-b] quinolin-4-yl)-N'-tricyclo[3.3.1.1$^{3,7}$]dec-1-yl-1,3-propane diamine which were found to be inactive in the interferon assay. Similar derivatives are disclosed in U.S. Pat. No. 4,013,665, issued Mar. 22, 1977.

Stein et al., J. Med. Chem. 1970, 13(1), 153–155, disclose a series 4-lower-alkylamino and 4-phenylamino-1,3-dimethyl-1H-pyrazolo[3,4-b]quinolines which were tested and found to exhibit no appreciable antimalarial activity.

Zikan et al., Chemical Abstracts 108:204613K, disclose 4-carboxyalkylamino-1,3-dimethyl-1H-pyrazolo[3,4-b] quinolines which are said to be useful as antiviral agents.

Zikan et al. Chemical Abstracts 106:138447q disclose a series of substituted 4-anilino-1,3-dimethyl-1H-pyrazolo[3, 4-b]-quinolines which are said to be useful as antiviral agents.

Radl et al., Chemical Abstracts 106:18429P, disclose a series of 1-substituted-4-(N-substituted amino)-3-methyl-1H-pyrazolo[3,4-b]quinolines which are said to be useful as potential antiviral agents. Specifically disclosed are N-[(4-methoxy-phenyl)methyl], N-(phenylmethyl), N-(2-phenylethyl) and N-cyclohexyl-1,3-dimethyl-1H-pyrazolo [3,4-b]quinolin-4-amines.

Radl et al., Chemical Abstracts 105:226434T, disclose a series of 4-hydroxyanilino and 4-alkoxyanilino-1,3-dimethyl-1H-pyrazolo[3,4-b]quinolines which are said to be useful as potential antiviral agents.

SUMMARY OF THE INVENTION

The invention relates to compounds of the Formula I:

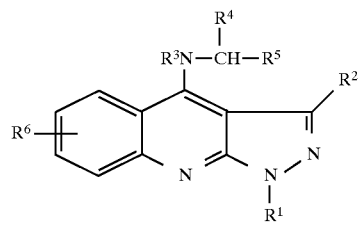

wherein:
$R^1$ is lower-alkyl;
$R^2$ is hydrogen, or lower-alkyl;
$R^3$ is hydrogen, or lower-alkyl;
$R^4$ is hydrogen, or lower-alkyl;
$R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and
$R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, an enantiomer or a racemic mixture thereof; with the proviso that when $R^1$ and $R^3$ are both methyl, and $R^3$, $R^4$, and $R^6$ are hydrogen, $R^5$ is other than 3-pyridinyl, 4-methoxyphenyl, phenyl, or phenylmethyl.

The compounds of the Formula I have been found to possess c-GMP-PDE V inhibitory activity and are thus useful (a) in the treatment of heart failure and/or hypertension, and (b) in combination with nitrates for reversing or reducing nitrate-induced tolerance and thus would be further useful in the treatment of angina pectoris, congestive heart disease and myocardial infarction.

Preferred compounds of Formula I above are those wherein:
$R^1$, R2 and $R^3$ are as defined hereinabove;
R4 is hydrogen;
$^5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R^4$ and $R^5$ together with the CH group to which they are bonded form an indanyl ring; and
$R^6$ is one substituent selected from the group consisting of hydrogen, lower-alkoxy, and hydroxy.

Particularly preferred compounds of Formula I above are those wherein:
$R^1$ is methyl, ethyl, or isopropyl;
$R^2$ is hydrogen, or methyl;
$R^3$ is hydrogen, or methyl;
$R^4$ is hydrogen;
$R^5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R^4$ and $R^5$ together with the CH group to which they are bonded form an indanyl ring; and $R^6$ is one substituent selected from the group consisting of hydrogen, methoxy, and hydroxy.

The most preferred compounds of the Formula I above are those wherein:

$R^1$, $R^2$, $R^3$, $R^4$ and $R^6$ are as defined directly above; and $R^5$ is phenyl (or phenyl substituted by from one to two, the same or different, substituents selected from the group consisting of methoxy, cyano, hydroxy, and 2-(4-morpholinyl)ethoxy), benzyl, 2-,3-,4-pyridinyl, or 2-furanyl; or $R^4$ and $R^5$ together with the CH group to which they are bonded form an indanyl ring; for example, N-(phenylmethyl)-1-ethyl-1H-pyrazolo[3,4-b]quinolin-4-amine;

N-(2-furanylmethyl)-1-ethyl-1H-pyrazolo[3,4-b]quinolin-4-amine; and

N-(4-methoxyphenylmethyl)-1-ethyl-6-methoxy-1H-pyrazolo[3,4-b]quinolin-4-amine.

The invention further relates to pharmaceutical compositions which comprise a compound of the formula I:

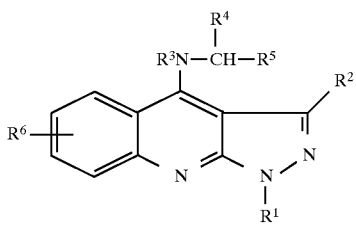

wherein:

$R^1$ is lower-alkyl;

$R^2$ is hydrogen, or lower-alkyl;

$R^3$ is hydrogen, or lower-alkyl;

$R^4$ is hydrogen, or lower-alkyl;

$R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and $R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, an enantiomer or a racemic mixture thereof; together with a pharmaceutically acceptable carrier, adjuvant, diluent, or vehicle.

The invention further relates to a method for effecting cGMP-phosphodiesterase inhibition in a mammalian organism which comprises administering to said organism an effective amount of a compound of the formula I:

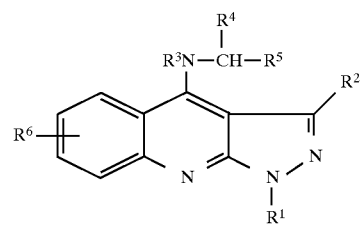

wherein:

$R^1$ is lower-alkyl;

$R^2$ is hydrogen, or lower-alkyl;

$R^3$ is hydrogen, or lower-alkyl;

$R^4$ is hydrogen, or lower-alkyl;

$R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and R6 is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, an enantiomer or a racemic mixture thereof.

The invention further relates to a method for treating heart failure and/or hypertension in a mammalian organism which comprises administering to said organism an effective amount of a compound of the formula I:

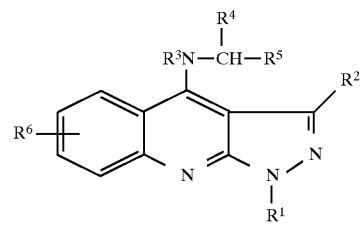

wherein:

$R^1$ is lower-alkyl;

$R^2$ is hydrogen, or lower-alkyl;

$R^3$ is hydrogen, or lower-alkyl;

$R^4$ is hydrogen, or lower-alkyl;

$R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and $R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, an enantiomer or a racemic mixture thereof.

The invention further relates to a method for reversing or reducing nitrate-induced tolerance in a mammalian organism undergoing nitrate therapy which comprises administering to said organism an effective amount of a compound of the formula I:

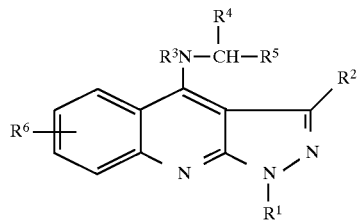

wherein:
- $R^1$ is lower-alkyl;
- $R^2$ is hydrogen, or lower-alkyl;
- $R^3$ is hydrogen, or lower-alkyl;
- $R^4$ is hydrogen, or lower-alkyl;
- $R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and
- $R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, an enantiomer or a racemic mixture thereof.

The invention further relates to a method for treating angina pectoris, congestive heart disease and myocardial infarction in a mammalian organism which comprises administering to said organism an effective amount of a compound of the formula I:

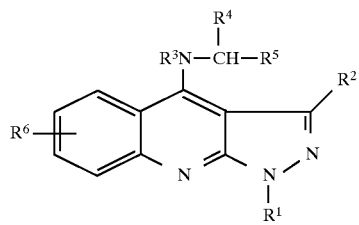

wherein:
- $R^1$ is lower-alkyl;
- $R^2$ is hydrogen, or lower-alkyl;
- $R^3$ is hydrogen, or lower-alkyl;
- $R^4$ is hydrogen, or lower-alkyl;
- $R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and
- $R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, an enantiomer or a racemic mixture thereof, in combination with a nitrate.

DETAILED DESCRIPTION INCLUSIVE OF PREFERRED EMBODIMENTS

The term lower-alkyl as used herein means linear or branched hydrocarbon chains having from one to about four carbon atoms and thus includes methyl, ethyl, propyl, isopropyl, n-butyl, sec-butyl, and the like.

The term lower-alkoxy as used herein means linear or branched alkyloxy substituents having from one to about four carbon atoms and thus includes methoxy, ethoxy, propoxy, isopropoxy, butoxy, sec-butoxy, and the like.

The term halogen, halide, or halo as used herein means bromine, chlorine, iodine or fluorine.

The synthesis of compounds of the invention may be outlined as shown in Scheme A:

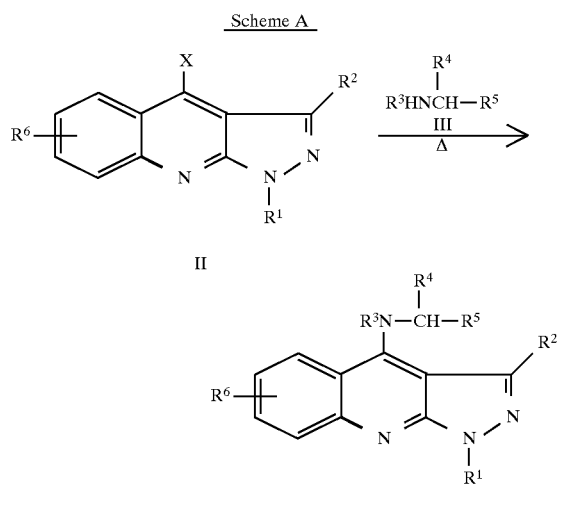

A suitably substituted 4-halo-1H-pyrazolo[3,4-b]quinoline of the formula II, wherein X is a halogen, preferably chlorine, in a suitable organic solvent, such as dimethylsulfoxide, is treated with at least one mole of a suitably substituted amine of the formula III, at a temperature in the range of about room temperature up to the boiling point of the solvent used, preferably at a temperature in the range of about 80° C. up to the boiling point of the solvent used, to afford the substituted 1H-pyrazolo[3,4-b]quinolin-4-amines of the formula I.

Simple chemical transformations which are conventional and well known to those skilled in the art of chemistry can be used for effecting changes in the functional groups of the compounds of the formula I. For example, the dealkylation of aryl ether derivatives to afford the corresponding phenol derivatives.

It will be appreciated that the compounds of the Formula I can possess an asymmetric carbon atom and are thus capable of existing as enantiomers. Unless otherwise specified herein, the invention is intended to extend to each of the enantiomeric forms, including the racemates. In some cases there may be advantages, i.e. greater potency, to using a particular enantiomer when compared to the other enantiomer or the racemate in the methods of the instant invention and such advantages can be readily determined by those skilled in the art. The separate enantiomers may be synthesized from chiral starting materials, or the racemates may be resolved by conventional procedures which are well known in the art of chemistry such as chiral chromatography, fractional crystallization of diastereomeric salts, and the like.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The suitably substituted 4-halo-1H-pyrazolo[3,4-b] quinolines of the formula II, which are required for the synthesis of the compounds of the formula I, can be prepared as shown in Scheme B:

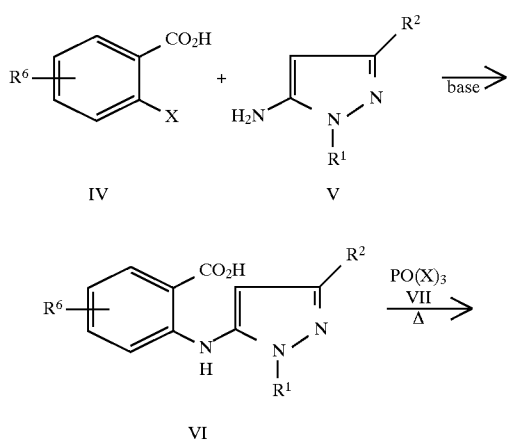

-continued
Scheme B

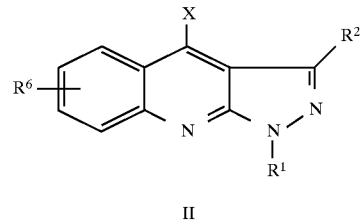

A suitably substituted benzoic acid derivative of the formula IV, wherein X is a halogen, preferably iodine, or bromine, in a suitable organic solvent, such as dimethylformamide, is treated with at least one mole of a suitable base, such as potassium carbonate, at least one mole of a suitably substituted pyrazole derivative of the formula V and a catalytic amount of $Cu(OAc)_2$ or copper, at a temperature in the range of about room temperature up to the boiling point of the solvent used, preferably at the boiling point of the solvent used, to afford the suitably substituted anthranilic acid derivatives of the formula VI. The suitably substituted anthranilic acid derivative of the formula VI can then be treated with an excess of a phosporous oxyhalide of the formula VII, wherein X is a halogen, preferably chlorine, at a temperature in the range of about room temperature up to the boiling point of the reaction mixture, preferably at a temperature in the range of about 90° C. up to the boiling point of the reaction mixture, to afford the compounds of the formula II.

The suitably substituted amines of the formula III, the suitably substituted benzoic acid derivatives of the formula IV and the suitably substituted pyrazole derivatives of the formula V are either commercially available, or they can be prepared by procedures known in the art, or by the procedures described hereinbelow in the examples.

The structures of the compounds of the invention were established by the mode of synthesis, and by one or more of elemental analysis, and infrared, nuclear magnetic resonance and mass spectroscopy. The course of the reactions and the identity and homogenity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected.

EXAMPLE 1

(a)

A mixture of 1-ethyl-4-chloro-1H-pyrazolo[3,4-b] quinoline (15.0 g, 0.065 mol), benzylamine (15.6 mL, 0.14 mol) and DMSO (100 mL) was heated at 80° C. overnight. The reaction mixture was poured into ice/water and the gummy solid which formed was collected by filtration. The solid was dissolved in ethyl acetate, dried over $MgSO_4$, filtered and concentrated. The residual oil was crystallized from ethyl acetate to afford 18 g (92%) of 1-ethyl-N-(phenyl methyl)-1H-pyrazolo[3,4-b]quinolin-4-amine, m.p. 130°–132° C.

(b)

1-Ethyl-N-(phenylmethyl)-1H-pyrazolo[3,4-b]quinolin-4-amine (1.0 g) was dissolved in warm methanol and was treated with an equimolar amount of methanesulfonic acid. The mixture was cooled in an ice-bath, then ether was added and the resulting solid was collected by filtration and recrystallized from isopropanol to afford 0.84 g of 1-ethyl-N-(phenylmethyl)-1H-pyrazolo[3,4-b]quinolin-4-amine.$CH_3SO_3H$, as a white solid, m.p. 255°–257° C.

EXAMPLE 2

(a)

To 2-iodobenzoic (250 g, 1.01 mol) in DMF (2 L) was added $K_2CO_3$ (154.8 g, 1.12 mol), then 5-amino-1-ethylpyrazole (112.3 g, 1.01 mol) and finally copper (II) acetate monohydrate (4.2 g, 0.021 mol). The reaction mixture was refluxed overnight and then the DMF was removed under reduced pressure. The residue was poured into ice-water (2 L) and the mixture was acidified with acetic acid to a pH of about 5–6. A precipitate formed which was collected by filtration, washed with water and dried in vacuo at 60°–70° C. to afford 278 g of N-(1-ethylpyrazol-5-yl) anthranilic acid.

(b)

A mixture of N-(1-ethylpyrazol-5-yl)anthranilic acid (278 g, 1.2 mol) and $POCl_3$ (550 g, 3.6 mol) was refluxed for 3 hours. The reaction mixture was cooled and then was poured into ice/water (3–4 L) . A solid formed which was collected by filtration and washed with water. The filtrate was extracted with $CH_2Cl_2$ (1 L) and the $CH_2Cl_2$ layer was evaporated to about 50 ml and both this solution and the previously isolated solid were purified by column chromatography on silica gel eluting with $CH_2Cl_2$ to afford 190 g (68%) of 1-ethyl-4-chloro-1H-pyrazolo[3,4-b]quinoline.

(c)

A mixture of 1-ethyl- 4-chloro-1H-pyrazolo[3,4-b] quinoline (11.6 g, 0.05 mol), DMSO (20 ml) and phenethylamine (12.1 g, 0.1 mol) was heated at 80° C. overnight. The reaction mixture was poured into water (1 L) and the precipitate which formed was collected by filtration and washed with water. The solid was dissolved in hot ethyl acetate, and then the solution was dried over $MgSO_4$, filtered and evaporated to a small volume. Hexane was added and then the mixture was cooled in an ice-bath and the product which crystallized was collected by fitration, washed with hexane and dried to afford 12.5 g of 1-ethyl-N-(phenylethyl)-1H-pyrazolo[3,4-b]quinoline-4 amine, m.p. 157°–158° C.

EXAMPLE 3

A mixture of 1-ethyl-4-chloro-1H-pyrazolo[3,4-b] quinoline (10 g, 0.043 mol), 4-methoxybenzylamine (13.0 g, 0.095 mol) and DMSO (75 ml) was heated at reflux overnight and then was allowed to stand for about 2 days. The reaction mixture was poured into ice-water and the resulting gum was treated with ethyl acetate. The product which oiled out of the ethyl acetate was separated and then was dissolved in $CH_2Cl_2$. The $CH_2Cl_2$ layer was washed with water, then brine and then was dried over $MgSO_4$ and evaporated under reduced pressure. The residue was dissolved in $CH_2Cl_2$ and purified by column chromatography on silica gel eluting with $CH_2Cl_2$ to afford the product as the free base. The free base was dissolved in methanol and then was treated with methanolic HCl. A precipitate formed which was collected by filtration, washed with ether and dried in vacuo at 50° C. to afford 12.4 g of 1-ethyl-N-(4-methoxy phenylmethyl)-1H-pyrazolo[3,4-b]quinolin-4-amine.HCl.½ $H_2O$, m.p. 179°–180° C.

EXAMPLE 4

(a)

To 2-iodobenzoic acid (54 g, 0.218 mol) in DMF (570 ml) was added $K_2CO_3$ (33.4 g, 0.242 mol), then 5-amino-1-isopropylpyrazole (27.3 g, 0.218 mol) and finally copper (II) acetate monohydrate (0.9 g, 4.5 mmol). The reaction mixture was refluxed overnight and then the DMF was evaporated. The residue was poured into ice/water and then the mixture was acidified with acetic acid and concentrated HCl to a pH of about 4. A precipitate formed which was collected by filtration, washed with water and dried in a vacuum oven at 40° C. to afford 52 g (97.2%) of N-(1-isopropylpyrazol-5-yl)anthranilic acid.

(b)

A mixture of N-(1-isopropylpyrazol-5-yl)anthranilic acid (52 g, 0.212 mol) and $POCl_3$ (436 ml, 4.68 mol) was refluxed for 3 hours, then was stirred at room temperature overnight. The excess $POCl_3$ was removed by distillation and then the residue was poured into ice/water. The mixture was neutralized with 35% NaOH and then extracted with $CH_2Cl_2$. The $CH_2Cl_2$ layer was separated and washed with water, then brine and then was dried over $MgSO_4$, filtered and evaporated. The residue was dissolved in $CH_2Cl_2$ and then was purified by column chromatography on silca gel eluting with $CH_2Cl_2$ to afford 21.3 g (40.9%) of 1-isopropyl-4-chloro-1H-pyrazolo[3,4-b]quinoline.

(c)

To a solution of 1-isopropyl-4-chloro-1H-pyrazolo[3,4-b] quinoline (10.6 g, 0.043 mol) in dimethylsulfoxide (75 ml) was added benzylamine (10.2 g, 0.095 mol). The reaction mixture was refluxed for 4.5 hours and then was allowed to stand at room temperature overnight. The reaction mixture was poured into ice/water and the precipitate which formed was collected by filtration and dissolved in $CH_2Cl_2$. The $CH_2Cl_2$ layer was washed with brine, dried over $MgSO_4$ and then evaporated in vacuo. The residue was dissolved in $CH_2Cl_2$ and purified by column chromatography on silca gel to afford, after recrystallization from hexane, 1-isopropyl-N-(phenylmethyl)-1H-pyrazolo[3,4-b]quinolin-4-amine, m.p. 162°–164° C.

EXAMPLE 5

(a)

2-Nitro-4-methoxybenzoic acid (43.4 g, 0.22 mol) in DMF (250 ml) was hydrogenated at 55 psi in the presence of 10% palladium on carbon (5.8 g) for 2.5 hours. The reaction mixture was filtered through SUPERCELL®, the filter cake was rinsed with ethanol and then the filtrate was poured into ice/water (3.5 L). A precipitate formed which was collected by filtration, washed with water and dried in an oven at 60° C. to afford 30.7 g (84%) of 4-methoxyanthranilic acid, m.p. 176°–178° C. (dec.).

(b)

A mixture of 4-methoxyanthranilic acid (30.5 g, 0.18 mol), water (274.5 ml), and concentrated HCl (36.6 ml) was heated at 75° C. to effect solution and then was cooled to 0° C. The mixture was then treated with $NaNO_2$ (13.3 g) in water (27.5 ml), followed by potassium iodide (45.75 g) in a water (75 ml)/$H_2SO_4$ (10.1 ml) solution. The reaction mixture was heated on a steam bath for 2 hours, then excess iodine was steam distilled. The reaction mixture was then cooled and the product was collected by filtration and dried in an oven at 75° C. To afford 39.28 g (78.6%) of crude product. The crude product was treated with toluene, the mixture was filtered and the filtrate was concentrated to afford 26.03 g of 2-iodo-4-methoxybenzoic acid.

(c)

$K_2CO_3$ (13.94 g, 0.101 mol) was dissolved in water (67 ml) and then 2-iodo-4-methoxybenzoic acid (25.3 g, 0.091 mol) was added, followed by 5-amino-1-ethylpyrazole (11.2 g, 0.101 mol) and finally copper (2.7 g). The reaction mixture was refluxed for 20 hours, cooled to room temperature and then water (350 ml) was added and the mixture was refluxed for 0.75 hours. The reaction mixture was cooled, and the product was collected by filtration, recrystallized from ethanol, and dried in an oven at 40° C. to afford 13.37 g (56%) of N-(1-ethylpyrazol-5-yl)-4-methoxyanthranilic acid, m.p. 130°–135° C.

(d)

A mixture of N-(1-ethylpyrazol-5-yl)-4-methoxyanthranilic acid (13.3 g, 0.051 mol) and $POCl_3$ (125 ml) was refluxed for 3 hours, then was allowed to sit overnight. The volume of $POCl_3$ was reduced, then ice/water, followed by $NH_4OH$ was added. A precipitate formed which was collected by filtration and dried in a vacuum oven at 50° C. to afford 11.51 g (87%) of 1-ethyl-4-chloro-7-methoxy-1H-pyrazolo[3,4-b]quinoline, m.p. 95°–98° C.

(e)

A mixture of 1-ethyl-4-chloro-7-methoxy-1H-pyrazolo[3,4b]quinoline (11.5 g, 0.044 mol), DMSO (70 ml) and benzylamine (10.56 ml, 0.095 mol) was heated on a steam bath for 18 hours. The reaction mixture was added to ice-water, and a solid formed which was collected by filtration, washed with water and dissolved in ethyl acetate. The ethyl acetate layer was dried over $MgSO_4$, filtered and evaporated. The residue was taken up in ether (500 ml), filtered and concentrated to afford 11.7 q of the product which was recrystallized from ether to afford 9.35 g of 1-ethyl-7-methoxy-N-(phenylethyl)-1H-pyrazolo[3,4-b]quinolin-4-amine, m.p. 163°–164.5° C.

EXAMPLE 6

1-Ethyl-7-methoxy-N-(phenylmethyl)-1H-pyrazolo[3,4-b]quinolin-4-amine (4 g, 0.012 mol) in DMF (70 ml) was treated with 60% NaH (2.4 g, 0.06 mol), followed by butane thiol (5.4 g, 0.06 mol). The reaction mixture was refluxed overnight and then was poured into ice-water. The mixture was acidified with 2N HCl and then was extracted with ethyl acetate (2×500 ml). The aqueous layer was treated with solid $NaHCO_3$ to adjust the pH to about 8, then the mixture was extratced with ethyl acetate (2×500 ml). The ethyl acetate layers were combined, washed with water, filtered and evaporated. The solid residue was recrystallized from ethyl acetate (2×) to afford 1.44 g of 1-ethyl-7-hydroxy-N-(phenylmethyl)-1H-pyrazolo[3,4-b]quinolin-4-amine, m.p. 252°–254° C.

EXAMPLE 7

A mixture of 1-ethyl-4-chloro-1H-pyrazolo[3,4-b]quinoline (1 g, 4.3 mmol), DMSO (3 ml) and veratylamine (1.3 ml, 8.6 mmol) was heated at 80°–90° C. for 2 hours. The reaction mixture was cooled, and then was poured into water. A gummy oil formed which crystallized upon the addition of a few drops of ether. The solid was collected by filtration, washed with water and recrystallized from ethyl acetate to afford 1.0 g of 1-ethyl-N-(3,4-dimethoxy phehylmethyl)-1H-pyrazolo[3,4-b]quinolin-4-amine, m.p. 169°–171° C.

EXAMPLE 8

A mixture of 1-ethyl-4-chloro-1H-pyrazolo[3,4-b]quinoline (1.0 g, 4.3 mmol), DMSO (3 ml) and 4-(aminomethyl)pyridine (0.92 ml, 9 mmol) was heated at 80°–90° C. overnight. The reaction mixture was poured into water (200 ml)/$NH_4OH$ (1 ml) and the mixture was extracted with $CH_2Cl_2$ (3×100 ml). The $CH_2Cl_2$ layers were combined, dried over $MgSO_4$ and evaporated. The residue was crystallized from ethyl acetate and recrystallized from ethyl acetate to afford 450 mg of 1-ethyl-N-(4-pyridinylmethyl)-1H-pyrazolo[3,4-b]quinolin-4-amine, m.p. 191°–192° C.

EXAMPLE 9

(a)

Hydrazine hydrate (32.5 ml, 0.67 mol) was added dropwise over 2–3 hours to a mixture of allyl cyanide (52 ml, 0.65 mol) and benzene (50 ml) while keeping the reaction temperature below 33° C. A solution of acetaldeyde (34.3 g, 0.78 mol) in benzene (100 ml) was then added dropwise to the reaction mixture and then the mixture was stirred at room temperature overnight. The benzene was evaporated and the residue was treated with butanol (250 ml) containing 1.5 g of dissolved sodium metal. The reaction mixture was refluxed for 5 hours, then was cooled to room temperature and was allowed to sit overnight. The butanol was evaporated in vacuo and the residue was purified by Kuglerohr distillation at 0.4 mm Hg and 100°–115° C. to afford the product as an oil which crystallized on standing to produce 7.8 g of 5-amino-1-ethyl-3-methylpyrazole, m.p. 95°–96° C.

(b)

A mixture of 5-amino-1-ethyl-3-methylpyrazole (7.5 g, 0.06 mol), 2-iodobenzoic acid (14.88 g, 0.06 mol), DMF (50 ml) $Cu(OAc)_2.H_2$ (0.5 g) and $K_2CO_3$ (8.3 g, 0.06 mol) was refluxed under a nitrogen atmosphere for 20 hours. The reaction mixture was cooled to room temperature and then was poured into ice-water. The mixture was neutralized with acetic acid and the resulting solid was collected by filtration, washed with water and dried to afford 7.1 g (48%) of N-(1-ethyl-3-methylpyrazol-5-yl)anthranilic acid.

(c)

A mixture of N-(1-ethyl-3-methylpyrazol-5-yl)anthranilic acid (7.0 g, 28.57 mmol) and $POCl_3$ (20 ml) was refluxed for 24 hours. The reaction mixture was cooled to room temperature and then was poured into ice-water. The mixture was neutralized with concentrated $NH_4OH$ to a pH of about 8 and the resulting gum crystallized slowly to afford a solid which was collected by filtration, washed with water and dried to afford 6.7 g (95%) of 1-ethyl-3-methyl-4-chloro-1H-pyrazolo[3,4-b]quinoline.

(d)

A mixture of 1-ethyl-3-methyl-4-chloro-1H-pyrazolo[3,4-b]quinoline (1.0 g, 4.3 mmol), DMSO (3 ml) and benzylamine (0.98 ml, 9 mmol) was heated at 80° C. overnight.

The reaction mixture was poured into water (100 ml), then NH$_4$OH (0.5 ml) was added. The mixture was extracted with CH$_2$Cl$_2$ (200 ml) and the CH$_2$Cl$_2$ was concentrated to about 20 ml and then this solution was purified by column chromatography on silica gel, followed by high pressure liquid chromatography eluting with 20% ethyl acetate/hexane to afford the product as the free base. The free base was dissolved in CH$_2$Cl$_2$ (20 ml) and treated with ethereal HCl. The mixture was evaporated and the residue was crystallized from ether to afford 0.9 g of 1-ethyl-3-methyl-N-(phenylmethyl)-1H-pyrazolo[3,4-b]quinolin-4amine.HCl, as an off white solid, m.p. 228°–231° C.

EXAMPLE 10

A mixture of 1-ethyl-4-chloro-1H-pyrazolo[3,4-b]quinoline (1.0 g, 4.3 mmol), DMSO (3 ml) and 4-cyanobenzylamine (1.2 g, 9 mmol) was heated on a steam bath for 3 hours, then was allowed to sit at room temperature overnight. The reaction mixture was poured into water and an oil separated. The oil was extracted with hot 10% ethanol/ethyl acetate, washed with water, and the organic layer was dried and evaporated. The residue was crystallized from ether/ethyl acetate and then was purified by recrystallization from ethyl acetate/hexane, followed by column chromatography on silca gel eluting with ethyl acetate and finally crystallization of the residue thus obtained from ethyl acetate/hexane to afford 280 mg of 1-ethyl-N-(4-cyanophenylmethyl)-1H-pyrazolo[3,4-b]quinolin-4-amine, as yellow crystals, m.p. 233°–234° C.

EXAMPLE 11

A mixture of 1-ethyl-4-chloro-1H-pyrazolo[3,4-b]quinoline (3.45 g, 0.015 mol), DMSO (12 ml) and 3-methoxybenzylamine (4.15 ml, 0.03 mol) was heated at 80°–90° C. for 3–4 hours. The reaction mixture was poured into water (300 ml) and then was extracted with ether (3×200 ml). The ether layers were combined, washed with water (200 ml), dried over MgSO$_4$ and evaporated. The residue was purified by column chromatography on silca gel eluting with ethyl acetate to afford 5.6 g of the product as the free base. The free base (1.0 g) was dissolved in ethanol and treated with ethanolic HCl. The ethanol was evaporated and ether and ethanol (2 ml) were added to the residue. The HCl salt was collected by filtration, washed with ether (25 ml) and dried in vacuo to afford 580 mg of 1-ethyl-N-(3-methoxyphenylmethyl)-1H-pyrazolo[3,4-b]quinolin-4amine, as a white solid, m.p. 260°–263° C.

EXAMPLE 12

(a)

A mixture of 2-iodobenzoic acid (14.9 g, 0.06 mol), 5-amino-1,3-dimethylpyrazole (6.7 g, 0.06 mol), DMF (125 ml), Cu(OAc)$_2$ (0,4 g) and K$_2$CO$_3$ (8.28 g, 0.06 mol) was refluxed overnight. The reaction mixture was poured into ice-water (500 ml) and then was acidified with acetic acid to a pH of about 5. The solid which formed was collected by filtration, washed with water (100 ml) and dried. The solid was dissolved in hot CHCl$_3$ (300 ml), filtered, dried over MgSO$_4$ and evaporated to about 20 ml. Hexane (50 ml) was added and then the product was collected by filtration, washed with hexane (30 ml) and dried to afford 6.2 g of N-(1,3-dimethyl-pyrazol-5-yl)anthranilic acid, m.p. 210°–211° C.

(b)

A mixture of N-(1,3-dimethyl-pyrazol-5-yl)anthranilic acid (7 g, 0.03 mol) and POCl$_3$ (40 ml) was heated on a steam bath for 3 hours. The reaction mixture was then poured into ice-water (600 ml) and then basified with NH$_4$H. The mixture was extracted with ether (3×200 ml) and the combined ether layers were dried over MgSO$_4$ and evaporated to afford 7.0 g of 1,3-dimethyl-4-chloro-1H-pyrazolo[3,4-b]quinoline, m.p. 127°–129° C.

(c)

A mixture of 1,3-dimethyl-4-chloro-1H-pyrazolo[3,4-b]quinoline (1.2 g, 0.005 mol), benzylamine (1.2 ml) and DMSO (3 ml) was heated at 80°–90° C. for 3–4 hours. The reaction mixture was cooled to room temperature and then was poured into water. The mixture was extracted with CH$_2$C$_2$ (3×50 ml) and then the CH$_2$Cl$_2$ layers were combined and evaporated. The residue was purified by column chromatography on silca gel eluting with ethyl acetate to afford the product which was crystallized from ether/hexane to afford 1.2 g of 1,3-dimethyl-N-(phenylmethyl)-1H-pyrazolo[3,4-b]quinolin-4-amine, as a yellow solid, m.p. 105° C.

EXAMPLE 13

A mixture of 1-ethyl-N-(3-methoxyphenylmethyl)-1H-pyrazolo[3,4-b]quinolin-4-amine (3.8 g, 0.0114 mol) and pyridine hydrochloride (10 g) was heated at about 200° C. for 3 hours. The reaction mixture was cooled and then 10% NaOH (70 mL) was added. The mixture was washed with ether (2×30 mL) and then the aqueous layer was acidified with acetic acid to a pH of about 5. The solid which formed was collected by filtration and dried in vacuo to afford 2.5–3 g of 1-ethyl-N-(3-hydroxyphenylmethyl)-1H-pyrazolo[3,4-b]quinolin-4-amine, as an off-white solid, m.p. 273°–275° C.

EXAMPLE 14

1-Ethyl-N-(3-hydroxyphenylmethyl)-1H-pyrazolo[3,4-b]quinolin-4-amine (350 mg) was dissolved in hot methanol (200 mL) and then 3 equivalents of methanesulfonic acid was added. The methanol was then evaporated to a volume of about 20 mL and one volume of ether was added. The solid which formed was collected by filtration, washed with ether and dried to afford 340 mg of 1-ethyl-N-(3-hydroxyphenylmethyl)-1H-pyrazolo[3,4-b]quinolin-4-amine.2 CH$_3$SO$_3$H, m.p. >240° C.

EXAMPLE 15

(a)

To a solution of 4-cyanophenol (5.95 g, 0.05 mol) in DMF (35 mL) at 0° C. was added 60% NaH (2.2 g, 0.055 mol). The reaction mixture was stirred at 0° C. for 15 minutes, then at room temperature for 15 minutes and then N-(2-chloroethyl)morpholine (prepared from 11.16 g, 0.06 mol of the hydrochloride salt) was added and the reaction mixture was stirred at room temperature for about 2 days. There was still a small amount of starting material present so the reaction mixture was heated on a steam bath for 4 hours. The reaction mixture was cooled to room temperature and then the solvent was removed. Ice-water was added to the residue and the solid which precipitated was collected by filtration and dried to afford 11.3 g (97%) of 4-[2-(4-morpholinyl)ethoxy]benzonitrile.

(b)

A mixture of 4-[2-(4-morpholinyl)ethoxy]benzonitrile (0.93 g, 4 mmol), ethanol (100 mL), CHCl$_3$ (4 mL) and PtO$_2$ (100 mg) was hydrogenated at 45 psi on a Parr hydrogenator for 8 hours. Concentrated HCl (2–3 drops) was then added to the reaction mixture and the hydrogenation was continued for another 10 hours. The catalyst was removed by filtration, the filter cake was washed with ethanol and then the filtrate was evaporated to dryness. The residue was dissolved in water and then was saturated with solid $K_2CO_3$. The mixture was extracted with $CH_2Cl_2$ and then the $CH_2Cl_2$ layer was dried over $K_2CO_3$ and evaporated to afford 0.75 g (79%) of 4-[2-(4-morpholinyl)ethoxy]phenylmethylamine.

(c)

A mixture of 1-ethyl-4-chloro-1H-pyrazolo[3,4-b]quinoline (0.7 g, 3 mmol), 4-[2-(4-morpholinyl)ethoxy]phenylmethylamine (0.75 g, 3.2 mmol) and DMSO (3 mL) was heated on a steam bath for 8 hours. Additional 1-ethyl-4-chloro-1H-pyrazolo[3,4-b]quinoline (0.7 g, 3 mmol) was then added and the reaction mixture was heated on a steam bath for another 4 hours. The reaction mixture was cooled to room temperature and then was poured into water. The mixture was extracted with $CH_2Cl_2$ (3×100 mL) and then $CH_2Cl_2$ layers were combined, dried over $MgSO_4$ and evaporated to dryness. The residue was purified by column chromatography on silica gel eluting with $CH_2Cl_2$/methanol (95/5), followed by recrystallization from ethyl acetate, to afford 1.0 g of 1-ethyl-N-[4-[2-(4-morpholinyl)ethoxy]phenylmethyl]-1H-pyrazolo[3,4-b]quinolin-4amine, as a yellow solid, m.p. 170°–172° C.

EXAMPLE 16

A mixture of 1-ethyl-4-chloro-1H-pyrazolo[3,4-b]quinoline (1.0 g, 0.0043 mol), DMSO (3 mL) and 2-aminomethylfuran (0.8 mL, 0.009 mol) was heated at 90° for 3 hours. The reaction mixture was then partitioned between $CH_2Cl_2$ (50 mL) and water (50 mL). The aqueous layer was separated and then extracted with $CH_2Cl_2$ (25 mL) and then the $CH_2Cl_2$ layers were combined, washed with water dried over $Na_2SO_4$ and reduced to a volume of about 3–5 mL. The solution was passed through a silica gel column eluting with ethyl acetate to afford the product which was recrystallized from ether/$CH_2Cl_2$ to afford 430 mg of 1-ethyl-N-(2-furanylmethyl)-1H-pyrazolo[3,4-b]quinolin-4-amine, as a yellow solid, m.p. 156°–158° C.

EXAMPLE 17

1-Ethyl-N-(2-furanylmethyl)-1H-pyrazolo[3,4-b]quinolin-4amine (1.3 g) was dissolved in methanol (10 mL) and then was treated with methanesulfonic acid (1 mL). The methanol was evaporated and the residue was crystallized from 2-propanol/ether and dried in vacuo to afford 1.12 g of 1-ethyl-N-(2-furanylmethyl)-1H-pyrazolo[3,4-b]quinolin-4-amine.$CH_3SO_3H$, m.p. 221°–222° C.

EXAMPLE 18

(a)

A mixture of 1-ethyl-N-(4-methoxyphenylmethyl)-1H-pyrazolo[3,4-b]quinolin-4-amine (7.0 g, 0.021 mol), boron tribromide (65 mL, 0.065 mol) and dichloroethane (250 mL) was stirred at room temperature for 1 hour and then was refluxed overnight. The reaction mixture was cooled and then was poured into ice-water (100 mL). An aqueous solution of NaOH was added to the mixture and then mixture was sonicated. The layers were separated and then the aqueous layer was washed with ether and then was acidified with acetic acid to pH of about 5–6. The precipitate which formed was collected by filtration to afford 5.6 g of the product as the free base. The free base (1.5 g) was then dissolved in hot methanol and 3–5 equivalents of methanesulfonic acid (2 mL) was added. The salt was then crystallized from ether/isopropanol and then collected by filtration to afford 850 mg of 1-ethyl-N-(4-hydroxyphenylmethyl)-1H-pyrazolo[3,4-b]quinolin-4-amine.$CH_3SO_3H$, m.p. 280° C. (dec.).

(b)

The free base (1.0 g) from example 18(a) was recrystallized from hot ether/THF (200 mL) and dried at 80° C. in vacuo to afford 220 mg of 1-ethyl-N-(4-hydroxyphenylmethyl)-1H-pyrazolo[3,4-b]quinolin-4-amine, m.p. 279°–280° C.

EXAMPLE 19

A mixture of 1-ethyl-4-chloro-1H-pyrazolo[3,4-b]quinoline (1.0 g, 0.0043 mol), DMSO (1 mL) and 3-aminomethylpyridine (0.97 mL, 0.0093 mol) was heated at 90° C. for 4 hours. The reaction mixture was poured into water and the solid which formed was collected by filtration and recrystallized from ether/$CH_2Cl_2$/hexane to afford the product as the free base. The free base was dissolved in methanol (100 mL) and then was treated with methanesulfonic acid (1 mL). The methanol was evaporated and then the residue was crystallized from 2-propanol/ether. The product was collected by filtration, washed with ether and dried in vacuo to afford 1.0 g of 1-ethyl-N-(3-pyridinylmethyl)-1H-pyrazolo[3,4-b]quinolin-4-amine.$2CH_3SO_3H$, m.p. 282°–284° C.

EXAMPLE 20

A mixture of 1-ethyl-4-chloro-1H-pyrazolo[3,4-b]quinoline (1.0 g, 0.0043 mol), DMSO (3 mL) and N-methylbenzylamine (1 mL, 0.009 mol) was heated at 90° C. for 4 hours. The reaction mixture was partitioned between $CH_2Cl_2$/water and then the $CH_2Cl_2$ layer was separated and evaporated. The residue was purified by column chromatography on silica gel eluting with ethyl acetate to afford 0.9 g of the product as the free base. The free base was dissolved in methanol (100 mL) and then was treated with methanesulfonic acid (1 mL). The methanol was evaporated and the residue was crystallized from 2-propanol/ether. The product was collected by filtration, washed with ether and dried in vacuo to afford 0.6 g of 1-ethyl-N-(methyl)-N-(phenylmethyl)-1H-pyrazolo[3,4-b]quinolin-4-amine.$CH_3SO_3H$, m.p. 175°–177° C.

EXAMPLE 21

A mixture of 1-ethyl-4-chloro-1H-pyrazolo[3,4-b]quinoline (1.0 g, 0.0043 mol), DMSO (3 mL) and 2-aminomethylpyridine (0.9 mL, 0.0086 mol) was heated at 110° C. overnight. The reaction mixture was cooled and then was poured into water. The mixture was extracted with $CH_2Cl_2$ and then the $CH_2Cl_2$ layer was evaporated. The residue was purified by column chromatography on silica gel eluting with 20% hexane/ethyl acetate to afford the product as the free base. The free base was then dissolved in methanol and was treated with methanesulfonic acid. The methanol was evaporated and the residue was recrystallized from 2-propanol/ether and dried in vacuo to afford 1.0 g of 1-ethyl-N-(2-pyridinylmethyl)-1H-pyrazolo[3,4-b]quinolin-4-amine.$2CH_3SO_3H$, as a yellow solid m.p. 259°–260° C.

EXAMPLE 22

A mixture of 1-ethyl-4-chloro-1H-pyrazolo[3,4-b]quinoline (1.0 g, 0.0043 mol), DMSO (3 mL) and 1-aminoindane (1 g) was heated at 110° C. for 16 hours. The reaction mixture was cooled and then was poured into water (100 mL). The solid which formed was collected by filtration and dried to afford the product as the free base. The free base was dissolved in methanol and then was treated with methanesulfonic acid. The methanol was evaporated and the residue was crystallized from hot methanol/2-propanol and then was recrystallized from hot methanol/2-propanol to afford 717 mg of 1-ethyl-N-(1-indanyl)-1H-pyrazolo[3,4-b]quinolin-4amine.CH$_3$SO$_3$H, m.p. 233°–235° C.

EXAMPLE 23

(a)

A mixture of 2-bromo-5-methoxybenzoic acid (141.5 g, 0.61 mol), 5-amino-1-ethylpyrazole (68 g, 0.61 mol), K$_2$CO$_3$ (84.2 g, 0.61 mol), DMF (500 mL) and Cu(OAc)$_2$ (3 g) was refluxed for about 2 days. The reaction mixture was cooled and then was poured into water (1500 mL). The mixture was acidified with acetic acid and the resulting solid was collected by filtration and dried to afford 110 g of N-(1-ethylpyrazol-5-yl)-5-methoxyanthranilic acid.

(b)

A mixture of N-(1-ethylpyrazol-5-yl)-5-methoxyanthranilic acid (110 g, 0.421 mol) and POCl$_3$ (300 mL) was refluxed overnight and then was allowed to stand at room temperature for about 3 days. The reaction mixture was poured into ice-water and then was basified with NH$_4$OH. The solid which formed was collected by filtration, washed with water and air dried to afford 100.5 g of 1-ethyl-4-chloro-6-methoxy-1H-pyrazolo[3,4-b]quinoline.

(c)

A mixture of 1-ethyl-4-chloro-6-methoxy-1H-pyrazolo[3,4b]quinoline (2.0 g, 7.66 mmol), DMSO (6 mL) and 4methoxybenzylamine (2.2 mL, 16.9 mmol) was heated at 110° C. overnight. The reaction mixture was cooled and then was poured into water. The mixture was extracted with ethyl acetate and then the ethyl acetate layer was dried over MgSO$_4$, filtered and evaporated. The residue was purified by column chromatography on silica gel eluting with ethyl acetate to afford 2.0 g of the product as the free base. The free base (1.0 g) was suspended in methanol and then was treated with methanesulfonic acid. The salt which precipitated was collected by filtration, recrystallized from methanol and dried in vacuo to afford 740 mg of 1-ethyl-6methoxy-N-(4-methoxyphenyl methyl)-1H-pyrazolo[3,4-b]quinolin-4amine.CH$_3$SO$_3$H, as a yellow solid, m.p. 263°–265° C.

EXAMPLE 24

A mixture of 1-ethyl-6-methoxy-N-(4-methoxyphenylmethyl)-1H-pyrazolo[3,4-b]quinolin-4-amine (1.0 g, 2.76 mmol), boron tribromide (6 mL, 6 mmol) and 1,2-ethylenedichloride (30 mL) was stirred at room temperature overnight. The reaction mixture was poured into water and then was basified with NaOH. The layers were separated and then the aqueous layer was acidified with acetic acid. The precipitate which formed was collected by filtration, washed with water and dried to afford the product as the free base. The free base was taken up in methanol and treated with methanesulfonic acid. The methanol was evaporated and the solid residue was recrystallized from 2-propanol/methanol/ether and dried in vacuo to afford 350 mg of 1-ethyl-6-hydroxy-N-(4-hydroxyphenyl methyl)-1H-pyrazolo[3,4-b]quinolin-4-amine.CH$_3$SO$_3$H.

Following a procedure similar to that described in Example 12(c), but substituting an appropriate compound of the Formula III for benzylamine, it is contemplated that the compounds of the Formula I illustrated in Examples 25–30 can be prepared.

EXAMPLE 25

1,3-Dimethyl-N- [S-(−)-1-(phenyl)ethyl]-1H-pyrazolo[3,4-b]quinolin-4-amine

EXAMPLE 26

1,3-Dimethyl-N-(4-chlorophenylmethyl)-1H-pyrazolo[3,4-b]quinolin-4-amine

EXAMPLE 27

1,3-Dimethyl-N-(3-methylphenylmethyl)-1H-pyrazolo[3,4-b]quinolin-4-amine

EXAMPLE 28

1,3-Dimethyl-N-(2-thienylmethyl)-1H-pyrazolo[3,4-b]quinolin-4-amine

EXAMPLE 29

1,3-Dimethyl-N-(2-pyrazinylmethyl)-1H-pyrazolo[3,4-b]quinolin-4-amine

EXAMPLE 30

1,3-Dimethyl-N-(5-isoxazolylmethyl)-1H-pyrazolo[3,4-b]quinolin-4-amine

EXAMPLE 31

Following procedures similar to those described in Examples 5(c)–5(e), but substituting 2-bromo-4-methylbenzoic acid for 2-iodo-4-methoxybenzoic acid in Example 5(c), it is contemplated that there can be prepared:

(a)

N-(1-Ethylpyrazol-5-yl)-4-methylanthranilic acid (b)

1-Ethyl-4-chloro-7-methyl-1H-pyrazolo[3,4-b]quinoline (c)

1-Ethyl-7-methyl-N-(phenylmethyl)-1H-pyrazolo[3,4-b]quinolin-4-amine

EXAMPLE 32

Following procedures similar to those described in Examples 5(c)–5(e), but substituting 2,6-dibromobenzoic acid for 2-iodo-4-methoxybenzoic acid in Example 5(c), it is contemplated that there can be prepared:

(a)

N-(1-Ethylpyrazol-5-yl)-5-bromoanthranilic acid (b)

1-Ethyl-4-chloro-6-bromo-1H-pyrazolo[3,4-b]quinoline (c)

1-Ethyl-6-bromo-N-(phenylmethyl)-1H-pyrazolo[3,4-b]quinolin-4-amine

Biological Test Results

In standard biological test procedures, the compounds of Formula I have been found to possess c-GMP-PDE V (formerly named as c-GMP-PDE I) inhibitory activity and are thus useful (a) in the treatment of heart failure and hypertension and (b) in combination with nitrates in reversing or reducing nitrate-induced tolerance and thus would be further useful in the treatment of angina pectoris, congestive heart disease and myocardial infarction.

Multiple isozymic forms of cyclic nucleotide phosphodiesterase (PDE) have been identified in mammalian cells. These isozymes hydrolyze cyclic adenosine monophosphate (cAMP) and/or cyclic guanosine monophosphate (cGMP) to the presumably biologically inactive 5'-nucleotide phosphates. Elevation of intracellular cGMP in vascular smooth muscle triggers a cascade of events that leads to a reduction in muscle tone while elevations in renal tubule cell cGMP stimulates natriuresis and diuresis. Vascular smooth muscle and renal cells contain a phosphodiesterase isozyme that has a low Km ($1 \mu M$) for the hydrolysis of cGMP. This isozyme has been referred to as the cGMP-PDE or cGMP-PDE V (formerly was named as cGMP-PDE I since it eluted from an anion-exchange sepharose resin in the first peak of PDE activity at a sodium acetate concentration between 150–200 mM). Thus inhibition of the cGMP-PDE isozyme is a viable subcellular mechanism by which increases in cGMP can produce a reduction in total peripheral resistance and a stimulation of natriuresis and diuresis. The development of cGMP-PDE inhibitors represents an approach for the discovery of agents useful for treating heart failure and hypertension. For example, compounds having high inhibitory potency for the cGMP-PDE are expected to lower blood pressure and induce natriuresis and diuresis.

The c-GMP-PDE V inhibitory activity of representative compounds of the invention was demonstrated by the following procedure.

The cGMP-PDE and other PDE isozymes were isolated from cardiovascular tissues (heart and aorta) of various animal species and man by anion-exchange and affinity chromatography as described by Silver et al., Sec. Messeng. Phos. 13:13–25, 1991; PDE activity, in the presence and absence of test compounds was determined essentially as described by Thompson et al., Adv. Cyclic Nucleotide Res. 10:69–92. To determine the potency and selectivity of compounds as PDE inhibitors, compounds are screened for their effect on cyclic nucleotide hydrolysis at $10 \mu M$. If $\geq 50\%$ inhibition of PDE activity is observed, an $IC_{50}$ value (concentration of compound causing 50% reduction in PDE activity) and corresponding 95% confidence intervals are generated. The $IC_{50}$ values are calculated from concentration-response curves as described by Tallarida and Murray, Manual of Pharmacologic Calculations with Computer Programs, Procedure 8, Graded Dose-response, pp. 14–19, Springer-Verlag, New York, 1981.

The following table summarizes the results obtained from the testing of representative compounds of the invention.

| Example No. | Percent Inhibition at Given $\mu M$ or $IC_{50}$ (nM) cGMP-PDE V |
|---|---|
| 1 (a) | 210 |
| 1 (b) | 2.23 |
| 2 (c) | 4200 |
| 3 | 89 |
| 4 (c) | 180 |
| 5 (e) | 85% (10 $\mu M$) or 54% (1 $\mu M$) or 14% (0.1 $\mu M$) |
| 6 | 85% (10 $\mu M$) or 50% (1 $\mu M$) |

-continued

| Example No. | Percent Inhibition at Given $\mu M$ or $IC_{50}$ (nM) cGMP-PDE V |
|---|---|
| | or 17% (0.1 $\mu M$) |
| 7 | 180 |
| 8 | 50% (10 $\mu M$) or 5% (1 $\mu M$) or 0% (0.1 $\mu M$) |
| 9 (d) | 170 |
| 10 | 57% (10 $\mu M$) or 0% (1 $\mu M$) |
| 11 | 450 |
| 12 (c) | 1140 |
| 13 | 150 |
| 14 | 86 |
| 15 (c) | 34% (10 $\mu M$) or 20% (1 $\mu M$) or 0% (0.1 $\mu M$) |
| 16 | 0.23 |
| 18 (a) | 91 |
| 18 (b) | 78% (10 $\mu M$) or 82% (1 $\mu M$) or 63% (0.1 $\mu M$) |
| 19 | 75% (10 $\mu M$) or 43% (1 $\mu M$) or 10% (0.1 $\mu M$) |
| 20 | 1260 |
| 21 | 97% (10 $\mu M$) or 58% (1 $\mu M$) or 27% (0.1 $\mu M$) |
| 22 | 94% (10 $\mu M$) or 75% (1 $\mu M$) or 34% (0.1 $\mu M$) |
| 23 (c) | 14 |
| 24 | 120 |

The antihypertensive activity of representative compounds of the invention was demonstrated by the following procedure.

Spontaneously hypertensive rats (SHR) were anesthetized with sodium pentobarbital (50 mg/kg, ip) and instrumented with catheters positioned in the inferior vena cava and abdominal aorta for administration of drug and recording of arterial pressure and heart rate, respectively. After a 2 day recovery from surgery, three baseline blood pressure measurements were made at 5 min intervals in conscious SHR. Compounds to be tested or vehicle were then administered intravenously in a dose-dependent manner (0.3–10 mg base/kg) while arterial pressure was recorded continuously on a polygraph. The mean arterial pressure response was measured 5 minutes after the administration of each dose of the test compound and the next dose given in a cumulative dose fashion. The response to each dose of the test compound was calculated as the difference from the mean of the three baseline measurements.

The following table summarizes the results obtained from the testing of representative compounds of the invention.

| Example No. | SHR iv % change in mean arterial pressure at Given mg/kg or $ED_{25}$ (mg/kg) |
|---|---|
| 1 (a) | 25 |
| 2 (c) | 16.5 |
| 16 | −16% (10 mg/kg) |
| 23 (c) | −7% (1 mg/kg) or −4% (3 mg/kg) |
| 24 | −15% (10 mg/kg) or −9% (3 mg/kg) or −10% (1 mg/kg) |

The activity of representative compounds of the invention in reversing or reducing nitrate-induced tolerance can be demonstrated by the following procedure:

Spontaneously hypertensive rats (17–25 weeks of age) are made nitroglycerin tolerant by repeated administration of high doses of nitroglycerin (100 mg/kg, s.c., 3 times/day for 3 consecutive days). To confirm tolerance challenge doses of nitroglycerin are administered intravenously at doses ranging from 1–300 μg/kg and the maximum change in mean arterial pressure (MAP) for each dose is recorded. Groups of tolerant rats are then pretreated with the compounds of the invention (tolerant pretreated group) or with vehicle (0.05N NaOH) (tolerant vehicle pretreated group) intravenously 5–10 minutes prior to administration of challenge doses of nitroglycerin. The administration of challenge doses of nitroglycerin to non-tolerant rats (the non-tolerant group) causes a dose-dependent decrease in MAP of between 10 to 40 mm Hg. The administration of challenge doses of nitroglycerin to the tolerant vehicle pretreated group results in a significant reduction of the hypotensive response. It is expected that the administration of challenge doses of nitroglycerin to tolerant rats which have been pretreated with the compounds of the invention (tolerant pretreated group) should result in varying degrees of restoration of the hypotensive response. The area under the dose-MAP curve is then calculated for the non-tolerant group and for the tolerant vehicle pretreated group and the tolerant pretreated group. The percent reversal of nitrate-induced tolerance is then calculated as follows:

Percent Reversal=(AUC$_{tol-pretreated}$-AUC$_{tol-veh}$)/(AUC$_{nontol}$-AUC$_{tol-veh}$)×100 wherein:

AUC$_{nontol}$=the area under the dose-MAP curve for the non-tolerant group.

AUC$_{tol-veh}$=the area under the dose-MAP curve for the tolerant vehicle pretreated group.

AUC$_{tol-pretreated}$=the area under the dose-MAP curve for the tolerant pretreated group.

A percent reversal of 100% or greater reflects complete reversal of nitrate-induced tolerance, whereas a percent reversal of 0% indicates that no reversal of nitrate-induced tolerance occurred.

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

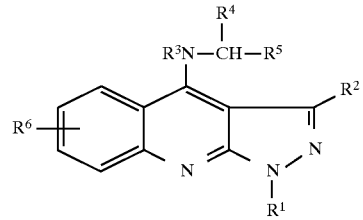

wherein:
   $R^1$ is lower-alkyl;
   $R^2$ is hydrogen, or lower-alkyl;
   $R^3$ is hydrogen, or lower-alkyl;
   $R^4$ is hydrogen, or lower-alkyl;
   $R^5$ is pyridazinyl, pyrazinyl, pyrimidinyl; or $R^4$ and $R^5$ together with the CH group to which they are bonded form an indanyl ring; and
   $R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or an enantiomer or a racemic mixture thereof.

2. A compound according to claim 1 wherein $R^4$ is hydrogen; and $R^6$ is one substituent selected from the group consisting of hydrogen, lower-alkoxy, and hydroxy.

3. A compound according to claim 1 wherein $R^4$ and $R^5$ together with the CH group to which they are bonded form and indanyl ring and $R^6$ is one substituent selected from the group consisting of hydrogen, lower-alkoxy and hydroxy.

4. A compound according to claim 3 wherein $R^1$ is methyl, ethyl, or isopropyl; and $R^2$ is hydrogen,or methyl.

5. A compound according to claim 4 wherein $R^3$ is hydrogen, or methyl; and $R^6$ is one substituent selected from the group consisting of hydrogen, methoxy, and hydroxy.

6. A pharmaceutical composition which comprises a compound of the formula:

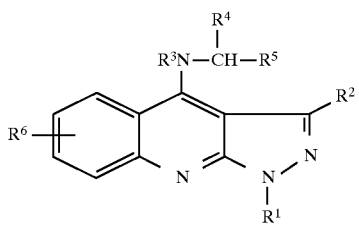

wherein:
$R^1$ is lower-alkyl;
$R^2$ is hydrogen, or lower-alkyl;
$R^3$ is hydrogen, or lower-alkyl;
$R^4$ is hydrogen, or lower-alkyl;
$R^5$ is pyridazinyl, pyrazinyl, and pyrimidinyl; or $R^4$ and $R^5$ together with the CH group to which they are bonded form an indanyl ring; and
$R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or an enantiomer or a racemic mixture thereof; together with a pharmaceutically acceptable carrier, adjuvant, diluent, or vehicle.

7. A pharmaceutical composition according to claim 6 wherein $R^4$ is hydrogen; and $R^6$ is one substituent selected from the group consisting of hydrogen, lower-alkoxy, and hydroxy.

8. A pharmaceutical composition according to claim 6 wherein $R^4$ and $R^5$ together with the CH group to which they are bonded form and indanyl ring and $R^6$ is one substituent selected from the group consisting of hydrogen, lower-alkoxy and hydroxy.

9. A pharmaceutical composition according to claim 8 wherein $R^1$ is methyl, ethyl, or isopropyl; and $R^2$ is hydrogen, or methyl.

10. A pharmaceutical composition according to claim 9 wherein $R^3$ is hydrogen, or methyl; and $R^6$ is one substituent selected from the group consisting of hydrogen, methoxy, and hydroxy.

11. A method for effecting cGMP-phosphodiesterase inhibition in a mammalian organism in need thereof which comprises administering to said organism a cGMP-phosphodiesterase inhibiting amount of a compound of the formula:

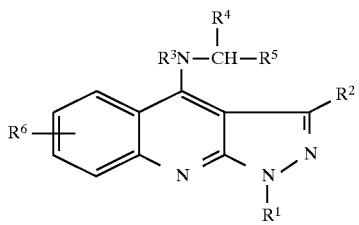

wherein:
$R^1$ is lower-alkyl;
$R^2$ is hydrogen, or lower-alkyl;
$R^3$ is hydrogen, or lower-alkyl;
$R^4$ is hydrogen, or lower-alkyl;
$R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and
$R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or an enantiomer or a racemic mixture thereof.

12. A method according to claim 11 wherein $R^4$ is hydrogen; and $R^6$ is one substituent selected from the group consisting of hydrogen, lower-alkoxy, and hydroxy.

13. A method according to claim 12 wherein $R^5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R^4$ and $R^5$ together with the CH group to which they are bonded form an indanyl ring.

14. A method according to claim 12 wherein $R^1$ is methyl, ethyl, or isopropyl; and $R^2$ is hydrogen,or methyl.

15. A method according to claim 14 wherein $R^3$ is hydrogen, or methyl; and $R^6$ is one substituent selected from the group consisting of hydrogen, methoxy, and hydroxy.

16. A method according to claim 15 wherein $R^5$ is phenyl (or phenyl substituted by from one to two, the same or different, substituents selected from the group consisting of methoxy, cyano, hydroxy, and 2-(4-morpholinyl)ethoxy), benzyl, 2-,3-,4-pyridinyl, or 2-furanyl; or $R^4$ and $R^5$ together with the CH group to which they are bonded form an indanyl ring.

17. A method according to claim 16 wherein the compound is selected from the group consisting of
  N-(phenylmethyl)-1-ethyl-1H-pyrazolo[3,4-b]quinolin-4-amine;
  N-(2-furanylmethyl)-1-ethyl-1H-pyrazolo[3,4-b]quinolin-4-amine; and
  N-(4-methoxyphenylmethyl)-1-ethyl-6-methoxy-1H-pyrazolo[3,4-b]quinolin-4-amine.

18. A method for treating heart failure and/or hypertension in a mammalian organism in need thereof which comprises administering to said organism a therapeutically effective amount of a compound of the formula;

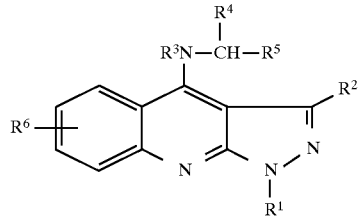

wherein:
$R^1$ is lower-alkyl;
$R^2$ is hydrogen, or lower-alkyl;
$R^3$ is hydrogen, or lower-alkyl;
$R^4$ is hydrogen, or lower-alkyl;
$R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and $R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or an enantiomer or a racemic mixture thereof.

19. A method according to claim 18 wherein $R^4$ is hydrogen; and $R^6$ is one substituent selected from the group consisting of hydrogen, lower-alkoxy, and hydroxy.

20. A method according to claim 19 wherein $R^5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R^4$ and $R^5$ together with the CH group to which they are bonded form an indanyl ring.

21. A method according to claim 20 wherein $R^1$ is methyl, ethyl, or isopropyl; and $R^2$ is hydrogen, or methyl.

22. A method according to claim 21 wherein $R^3$ is hydrogen, or methyl; and $R^6$ is one substituent selected from the group consisting of hydrogen, methoxy, and hydroxy.

23. A method according to claim 22 wherein $R^5$ is phenyl (or phenyl substituted by from one to two, the same or different, substituents selected from the group consisting of methoxy, cyano, hydroxy, and 2-(4-morpholinyl)ethoxy), benzyl, 2-,3-,4-pyridinyl, or 2-furanyl; or $R^4$ and $R^5$ together with the CH group to which they are bonded form an indanyl ring.

24. A method according to claim 23 wherein the compound is selected from the group consisting of N-(phenylmethyl)-1-ethyl-1H-pyrazolo[3,4-b]quinolin-4-amine;

N-(2-furanylmethyl)-1-ethyl-1H-pyrazolo[3,4-b]quinolin-4-amine; and

N-(4-methoxyphenylmethyl)-1-ethyl-6-methoxy-1H-pyrazolo [3,4-b]quinolin-4-amine.

25. A method for treating angina pectoris, congestive heart disease or myocardial infarction in a mammalian organism in need thereof which comprises administering to said organism a therapeutically effective amount of a compound of the formula:

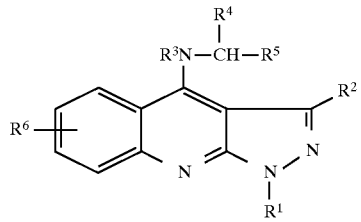

wherein:

$R^1$ is lower-alkyl;

$R^2$ is hydrogen, or lower-alkyl;

$R^3$ is hydrogen, or lower-alkyl;

$R^4$ is hydrogen, or lower-alkyl;

$R^5$ is phenyl (or phenyl substituted by from one to three, the same or different, substituents selected from the group consisting of lower-alkoxy, cyano, hydroxy, 4-morpholinyllower-alkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R^4$ and $R^5$ together with the CH group to which they are bonded form an indanyl ring; and $R^6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or an enantiomer or a racemic mixture thereof, in combination with a nitrate.

26. A method according to claim 25 wherein $R^4$ is hydrogen; and $R^6$ is one substituent selected from the group consisting of hydrogen, lower-alkoxy, and hydroxy.

27. A method according to claim 26 wherein $R^5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R^4$ and $R^5$ together with the CH group to which they are bonded form an indanyl ring.

28. A method according to claim 27 wherein $R^1$ is methyl, ethyl, or isopropyl; and $R^2$ is hydrogen, or methyl.

29. A method according to claim 28 wherein $R^3$ is hydrogen, or methyl; and $R^6$ is one substituent selected from the group consisting of hydrogen, methoxy, and hydroxy.

30. A method according to claim 29 wherein $R^5$ is phenyl (or phenyl substituted by from one to two, the same or different, substituents selected from the group consisting of methoxy, cyano, hydroxy, and 2-(4-morpholinyl)ethoxy), benzyl, 2-,3-,4-pyridinyl, or 2-furanyl; or $R^4$ and $R^5$ together with the CH group to which they are bonded form an indanyl ring.

31. A method according to claim 30 wherein the compound is selected from the group consisting of N-(phenylmethyl)-1-ethyl-1H-pyrazolo[3,4-b]quinolin-4-amine;

N-(2-furanylmethyl)-1-ethyl-1H-pyrazolo[3,4-b]quinolin-4-amine; and

N-(4-methoxyphenylmethyl)-1-ethyl-6-methoxy-1H-pyrazolo [3,4-b]quinolin-4-amine.

* * * * *